(12) United States Patent
Warner et al.

(10) Patent No.: US 10,372,874 B2
(45) Date of Patent: Aug. 6, 2019

(54) MACRO-ENABLED DISPLAY ELEMENTS

(71) Applicant: General Electric Company, Schenectady, NY (US)

(72) Inventors: Adrian F. Warner, Delafield, WI (US); Joseph John Manak, Albany, NY (US); Jeffrey Wayne Eberhard, Albany, NY (US); Daniel Richard Schneidewend, Menomonee Falls, WI (US); Hao Lai, Rexford, NY (US)

(73) Assignee: General Electric Company, Schednectady, NY (US)

( * ) Notice: Subject to any disclaimer, the term of this patent is extended or adjusted under 35 U.S.C. 154(b) by 474 days.

(21) Appl. No.: 14/462,437

(22) Filed: Aug. 18, 2014

(65) Prior Publication Data
US 2016/0048635 A1 Feb. 18, 2016

(51) Int. Cl.
*G06F 19/00* (2018.01)
*G06F 3/0484* (2013.01)
*G16H 30/00* (2018.01)
*G06F 3/0488* (2013.01)

(52) U.S. Cl.
CPC .......... *G06F 19/321* (2013.01); *G06F 3/0488* (2013.01); *G06F 3/04842* (2013.01); *G16H 30/00* (2018.01); *G06F 2203/04803* (2013.01); *G06F 2203/04806* (2013.01)

(58) Field of Classification Search
CPC .. G06F 19/321; G06F 19/3418; G06F 19/322; G06F 3/0488; G06F 3/04842; G06F 2203/04803; G06F 2203/04806; A61B 5/743
See application file for complete search history.

(56) References Cited

U.S. PATENT DOCUMENTS

| 4,553,205 | A | 11/1985 | Porchia |
| 7,571,431 | B2 | 8/2009 | Hampapuram et al. |
| 8,270,003 | B2 | 9/2012 | Lum et al. |
| 8,370,863 | B2 | 2/2013 | Grigoriev et al. |
| 2009/0135194 | A1* | 5/2009 | Keuenhof ............. G06F 19/321 345/581 |

(Continued)

FOREIGN PATENT DOCUMENTS

| EP | 2161899 A1 | 3/2010 |
| EP | 2628442 A1 | 8/2013 |

(Continued)

OTHER PUBLICATIONS

The American Heritage Dictionary, "American Heritage Dictionary Entry: input", <URL https://www.ahdictionary.com/word/search.html?q=input/>, p. 1-3.*

*Primary Examiner* — Ajay M Bhatia
*Assistant Examiner* — Mong-Shune Chung
(74) *Attorney, Agent, or Firm* — McCoy Russell LLP

(57) ABSTRACT

Embodiments for aggregating multiple data sources on a single display device are provided. In one example, a computing device comprises at least one input configured to receive data from one or more data sources, a user interface to receive user input, and instructions to identify an event of a procedure based on one or more of data received from the one or more data sources and user input received via the user interface, and arrange one or more display information elements on a display device based on the identified event and a workflow protocol.

19 Claims, 10 Drawing Sheets

(56) References Cited

U.S. PATENT DOCUMENTS

| | | | |
|---|---|---|---|
| 2011/0201900 A1* | 8/2011 | Zhang | G06F 19/3487 600/300 |
| 2012/0331138 A1 | 12/2012 | Sun et al. | |
| 2013/0024787 A1 | 1/2013 | Polis et al. | |
| 2014/0282053 A1* | 9/2014 | Hauschild | G06F 3/0481 715/744 |
| 2015/0332196 A1* | 11/2015 | Stiller | G06Q 10/06316 705/2 |

FOREIGN PATENT DOCUMENTS

| | | |
|---|---|---|
| WO | 0008548 A1 | 2/2000 |
| WO | 0148677 A2 | 7/2001 |
| WO | 03081477 A1 | 10/2003 |
| WO | 2008034108 A1 | 3/2008 |
| WO | 2009009497 A1 | 1/2009 |
| WO | 2009117149 A2 | 9/2009 |
| WO | 2012048468 A1 | 4/2012 |

\* cited by examiner

MACRO-ENABLED DISPLAY ELEMENTS

FIELD OF THE INVENTION

Embodiments of the subject matter disclosed herein relate to aggregating multiple data sources on a single display device.

BACKGROUND

Healthcare procedures are becoming increasingly complex, and may frequently include multiple sensors, devices, and imaging systems that may be monitored by one or more practitioners during a procedure. In some examples, representations of multiple data signals from the sensors, devices, and imaging systems may be displayed on a single display device. However, if a practitioner desires to change an arrangement of the displayed elements, he or she may have to manually adjust the arrangement displayed elements, reducing efficiency of the workflow during the procedure.

BRIEF DESCRIPTION

In one embodiment, a computing device comprises at least one input configured to receive data from one or more data sources, a user interface to receive user input, and instructions to identify an event of a procedure based on one or more of data received from the one or more data sources and user input received via the user interface, and arrange one or more display information elements on a display device based on the identified event and a workflow protocol.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE FIGURES

The present invention will be better understood from reading the following description of non-limiting embodiments, with reference to the attached drawings, wherein below.

DETAILED DESCRIPTION

The following description relates to various embodiments for identifying an event of a procedure and arranging one or more display information elements on a display device based on the identified event and a workflow protocol. The event may be identified based on one or more of data received from one or more data sources and user input received via a user interface, for example. The procedure may be a medical procedure, and each of the one or more data sources may send data relating to the procedure. The workflow protocol may define a series of events to be performed during the procedure and include one or more predefined arrangements of elements on the display device, each arrangement corresponding to a given event of the procedure. In this way, display format presentation control may be enabled when aggregating multiple system displays into one display screen, when all such devices are involved in the delivery of a common healthcare procedure, allowing a user to make the display context sensitive to the demands of the procedure.

Figure 1:
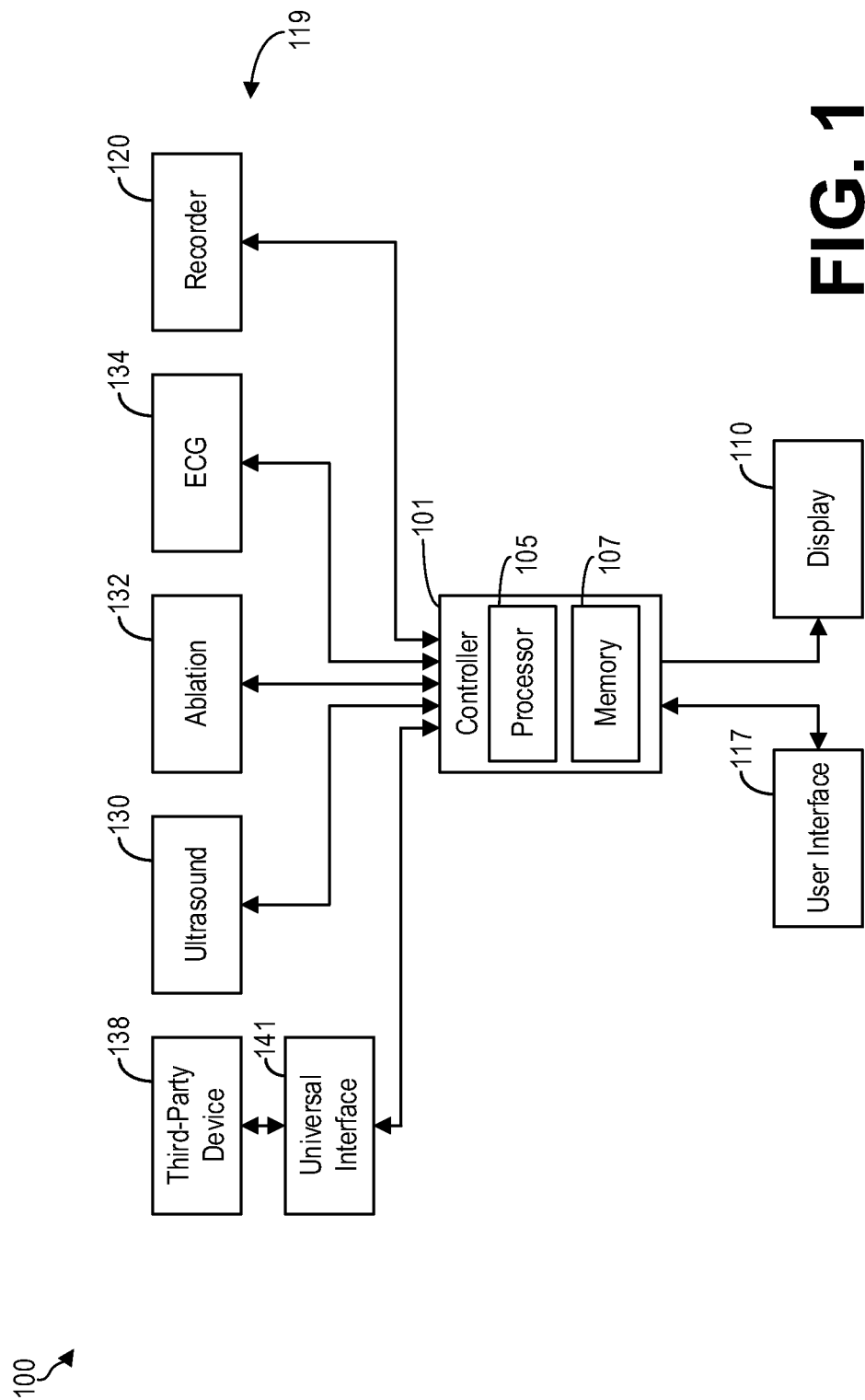
FIG. 1 shows a schematic diagram of a multi-element display system.
Figure 6:
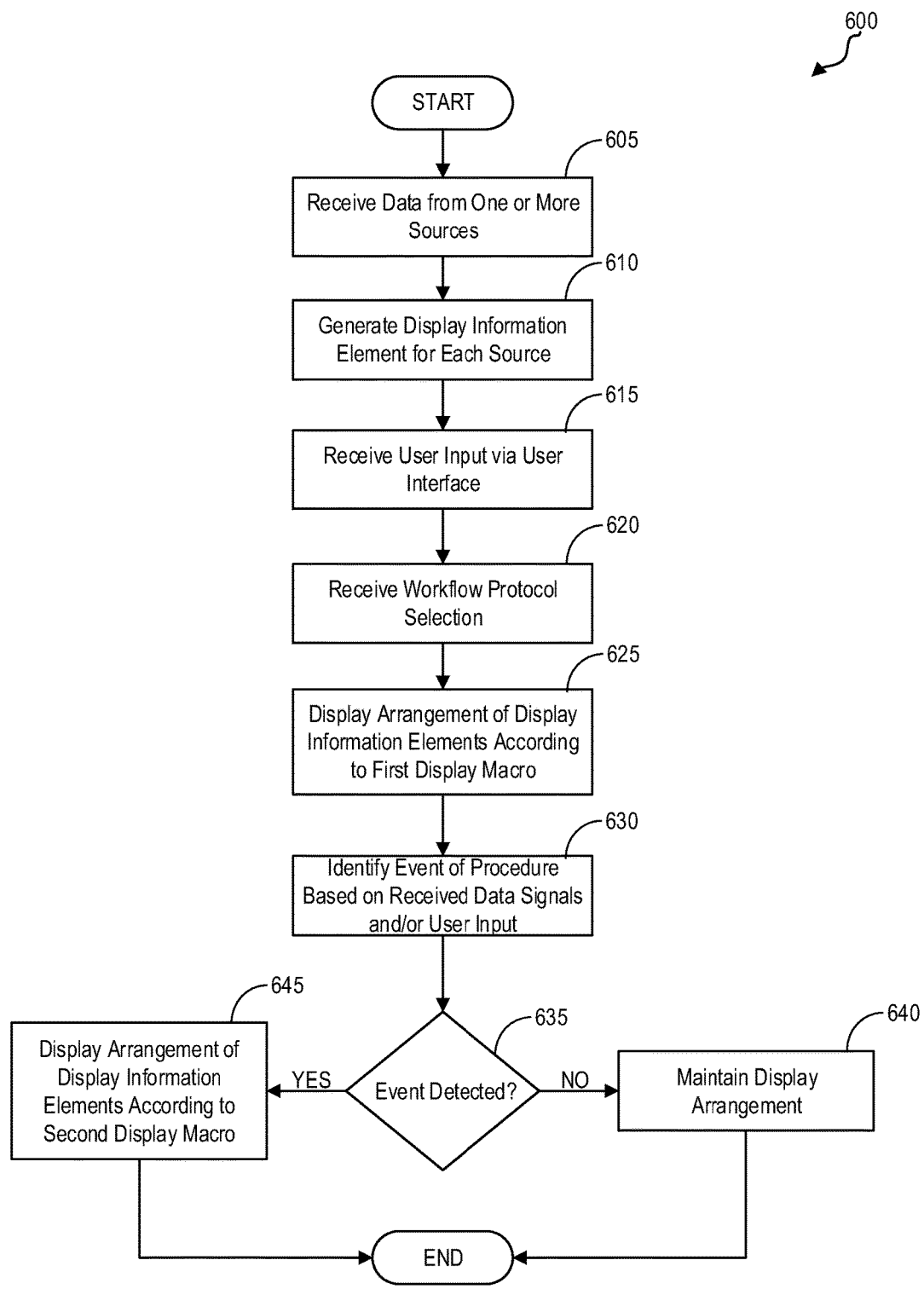
FIG. 6 shows a high-level flow chart illustrating an example method for aggregating video from a plurality of data sources on a single display screen.
Figure 7:
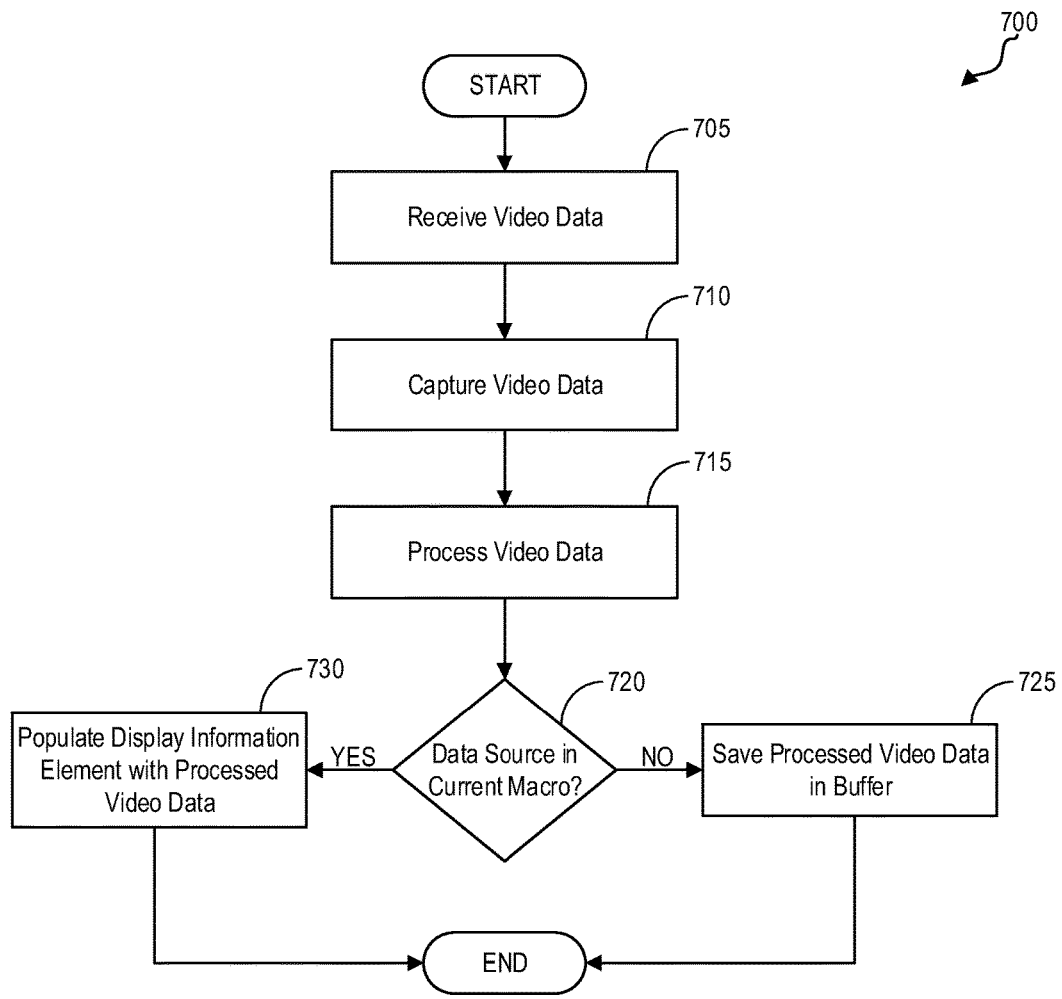
FIG. 7 shows a high-level flow chart illustrating an example method for populating a display information element with video from an external data source.
Figure 8:
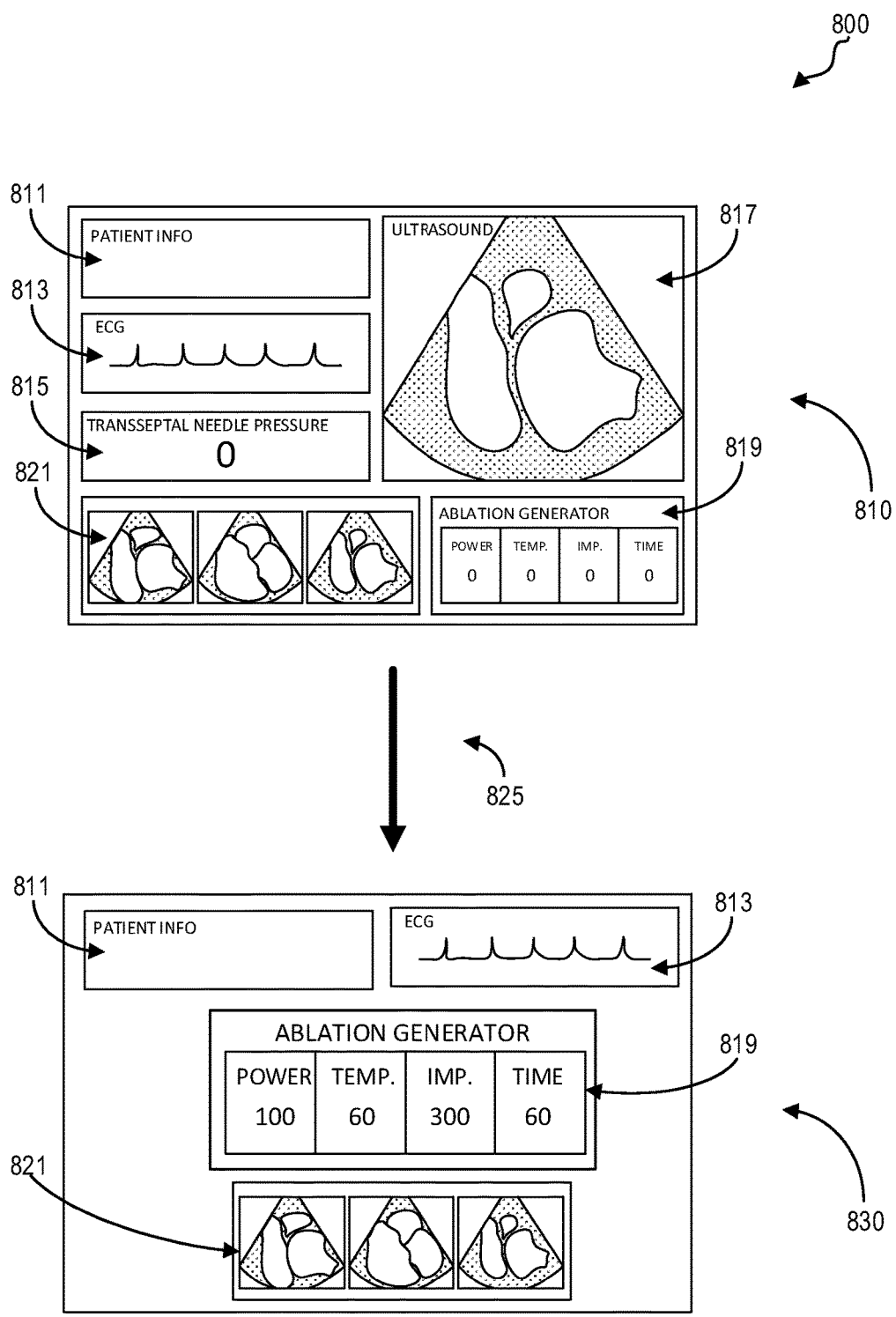
FIG. 8 shows an example transition between display device element arrangements on a multi-element display screen.
Figure 9:
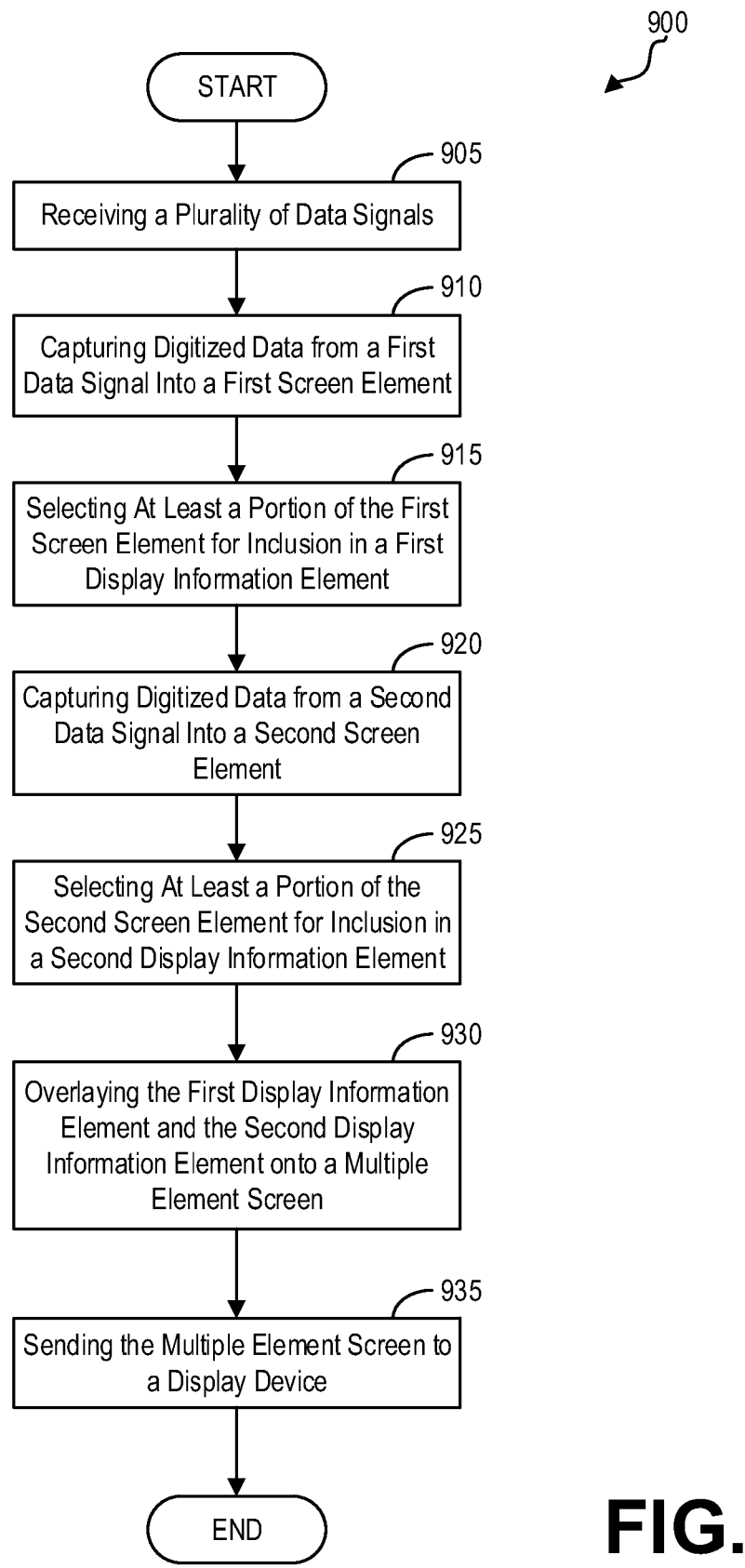
FIG. 9 shows a high-level flow chart illustrating an example method for aggregating video from multiple, dissimilar sources into a single display.

The workflow protocol may be executed by a computing device included in a multi-element display system, as illustrated in FIG. 1. FIGS. 2-5 show example multi-element display screens illustrating example aggregation of multiple system displays into one display screen. FIGS. 6-7 and 9 are methods that may be executed by the computing device of FIG. 1. FIG. 8 shows an example transition between display device element arrangements during the execution of the method of FIG. 6.

Figure 10:
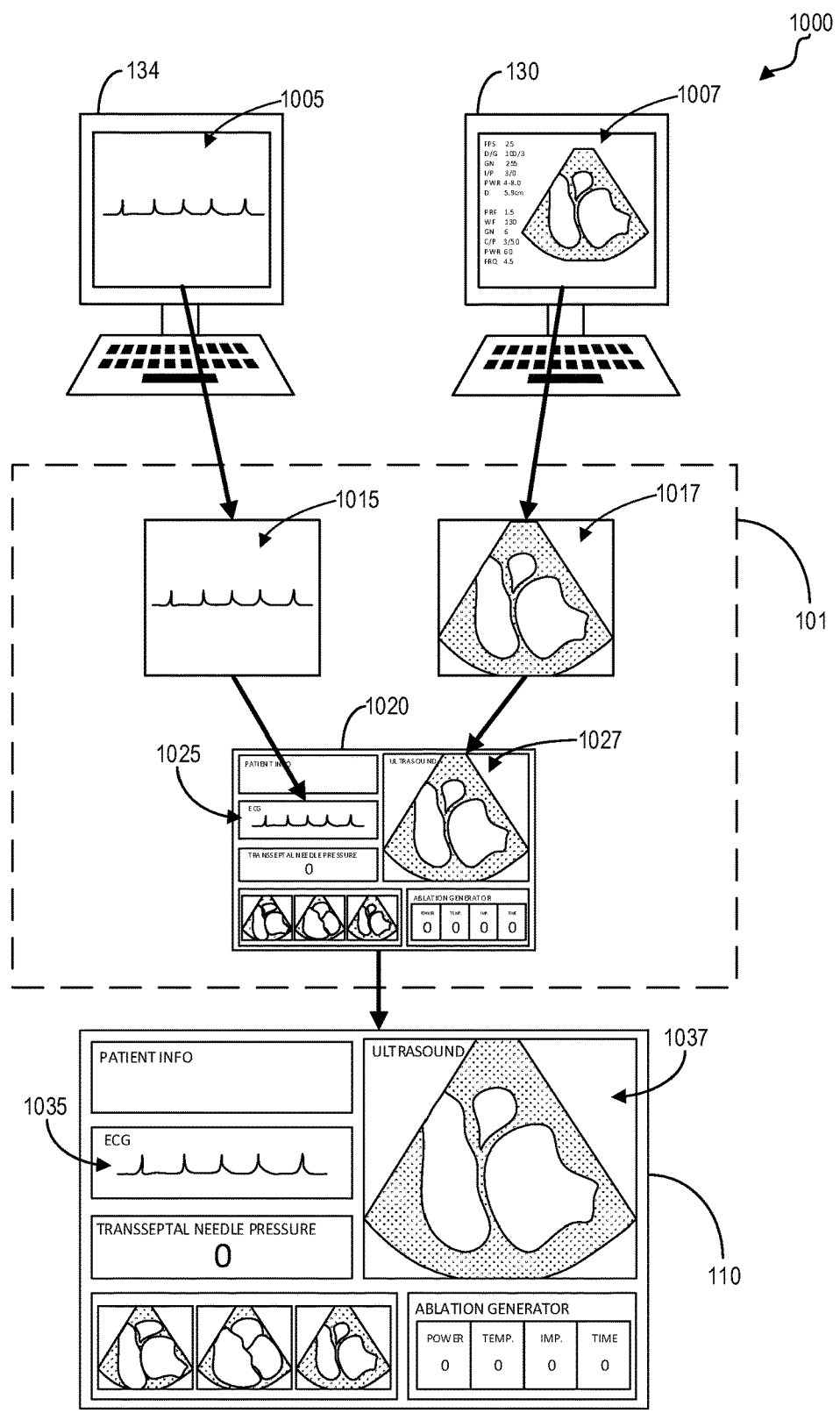
FIG. 10 shows a pictorial diagram illustrating the method of FIG. 9.

FIG. 10 is a diagram illustrating an aggregation according to the method of FIG. 9.

FIG. 1 is a schematic diagram of a multi-element display system 100 in accordance with an embodiment of the invention. The multi-element display system 100 includes a computing device, herein referred to as a display controller 101, that aggregates video and other data from multiple, dissimilar source systems 119 on a display 110. The controller 101 may treat data from source systems 119 as individual information elements, which can be moved, scaled, and aggregated independent of the original display context and independent of the source display system.

Display controller 101 may include a logic machine, such as processor 105. Processor 105 may include one or more physical devices configured to execute instructions. For example, processor 105 may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The processor 105 is in electronic communication with the data sources 119. For the purposes of this disclosure, the term "electronic communication" may be defined to include both wired and wireless communications. The processor is also in electronic communication with a display 110, and the processor 105 may process the data from data sources 119 into images for display on the display 110. The processor 105 may include a central processor (CPU) according to an embodiment. According to other embodiments, the processor 105 may include other electronic components capable of carrying out processing functions, such as a digital signal processor, a field-programmable gate array (FPGA), or a graphic board. According to other embodiments, the processor 105 may include multiple electronic components capable of carrying out processing functions. For example, the processor 105 may include two or more electronic components selected from a list of electronic components including: a central processor, a digital signal processor, a field-programmable gate array, and a graphic board. According to another embodiment, the processor 105 may also include a complex demodulator (not shown) that demodulates RF data from data sources 119 and generates raw data. In another embodiment the demodulation can be carried out earlier in the processing chain.

The processor 105 is adapted to perform one or more processing operations according to a plurality of selectable modalities on data from data sources 119. The data may be processed in real-time during a medical procedure as the data is received from data sources 119. For the purposes of this disclosure, the term "real-time" is defined to include a procedure that is performed without any intentional delay. The data may be stored temporarily in a buffer (not shown) during a medical procedure and processed in less than real-time in a live or off-line operation. Some embodiments of the invention may include multiple processors (not shown) to handle the processing tasks that are handled by processor 105 according to the exemplary embodiment described hereinabove. For example, a first processor may be utilized to demodulate and decimate an RF signal while a second processor may be used to further process the data prior to displaying an image. It should be appreciated that other embodiments may use a different arrangement of processors.

Display controller 101 may further include a storage machine, such as memory 107, configured to hold instructions executable by processor 113 to implement the methods and processes described herein. When such methods and processes are implemented, the state of memory 107 may be transformed—for example, to hold different data. The memory 107 may comprise any known data storage medium. Memory 107 may include removable and/or built-in devices. Memory 107 may include optical memory (for example, CD, DVD, HD-DVD, Blu-Ray Disc, etc.), semiconductor memory (for example, RAM, EPROM, EEPROM, etc.), and/or magnetic memory (for example, hard-disk drive, floppy-disk drive, tape drive, MRAM, etc.), among others. Memory 107 may include volatile, nonvolatile, dynamic, static, read/write, read-only, random-access, sequential-access, location-addressable, file-addressable, and/or content-addressable devices.

Multi-element display system 100 may include data sources 119 comprising a plurality of dissimilar source systems. For example, data sources 119 may include an ultrasound system 130, an ablation generator 132, an echocardiograph system 134, a recording system 120 (e.g., a recorder), an x-ray device (not shown), and one or more third-party devices 138. One or more of the data sources 119 may be connected to controller 101 via a universal interface 141. Data sources 119 may further include a plurality of sensors to monitor quantities such as pressure, temperature, and so on. Data sources 119 may further include monitoring devices not shown such as an endoscope, a pulse oximeter, a noninvasive blood pressure amplifier, gas analysis systems, and the like. In general, data sources 119 may include any medical device that outputs a data signal in any form.

Multi-element display system 100 may include video and/or screen capture technology in order to treat video from data sources 119 as individual information elements. For example, an analog signal from one or more of the data sources 119 may be digitized by an analog-to-digital converter to produce a digital data stream. The digital data stream may then be processed, modified, and/or encoded to prepare the digitized video for display. For example, the data stream may be captured into a screen element and at least a portion of the screen element may be included in a display information element placed in a multiple element screen that is displayed on a display device.

Video information from data sources 119 may be transmitted as uncompressed video in order to provide the highest quality video signal possible for display. In some examples, one or more data sources 119 may include components for analog-to-digital conversion such that a data source provides a digital information signal ready for processing.

Each data source 119 may be connected to display controller 101 via a specified interface. For example, each data source 119 may be connected to controller 101 via a high-definition multimedia interface (HDMI), digital visual interface (DVI), serial digital interface (SDI), FireWire, DisplayPort, video graphics array (VGA), composite interface, S-video, component, or any audio/video interface for transferring compressed or uncompressed video data and/or compressed or uncompressed audio data. In some examples, data sources 119 may include one or more third-party devices 138 that may be incapable of directly interfacing with controller 101. In such examples, a universal interface 141 may enable electronic communication between a third-party device 138 and controller 101.

As discussed herein, some data sources 119 may provide video signals, such as ultrasound system 130 or an endoscope. However, some data sources 119 may provide other forms of real-time data signals other than video. For example, a signal from a pressure sensor may not comprise a video signal, however the pressure signal may be displayed in graph form as a function of time, as an instantaneous pressure value, a combination thereof, and so on.

A user interface 117 may be used to control operation of the display controller 101, including, for example, to control the input of patient data, to change a display parameter, to define a plurality of display layouts, and the like. The user interface 117 may include one or more of the following: a keyboard, a mouse, a rotary, a trackball, hard keys linked to specific actions, soft keys that may be configured to control different functions, a camera, a microphone, a speaker, a touch pad, a foot pedal linked to specific actions, and a graphical user interface displayed on a display device, such as display 110. In one example, a camera (not shown) may be used to identify when a user is looking at a display 110 and subsequently track the gaze of the user, so that display controller 101 may accordingly adjust an arrangement of elements on display 110 to emphasize the element gazed upon by the user. In another example, a microphone (not shown) may be used for voice control of an arrangement of elements on display 110. For example, controller 101 may use the microphone to detect a voice command to display a particular element or to display a specified arrangement of elements. In another example, a foot pedal (not shown) may be used for controlling an arrangement of elements or the size of an element on display 110. For example, the foot pedal may include clickable switches for selecting different arrangements of elements or control modes, and may further include a variable controller that may increase/decrease, for example, the size of a displayed element, the granularity of the arrangement of elements, and so on.

Multi-element display system 100 may include a display 110 comprising one or more display screens for displaying a variety of aggregated data from data sources 119. For example, display 110 may include a large display screen located in, for example, an operating room or medical laboratory. Display 110 may comprise a liquid-crystal display (LCD), a light-emitting diode (LED) display, an organic light-emitting diode (OLED) display, an electroluminescent display (ELD), a plasma display, a cathode ray tube (CRT) display, and so on. Furthermore, display 110 may include one or more display monitors for displaying a graphical user interface 117. Such display monitors may be used when, for example, controlling display controller 101.

Controller 101 may capture the data from each data source 119 into a display information element. A display information element encapsulates the data from a data source 119. Each data source 119 may visually render data via data-dependent rendering methods such as graphing, grid display, and so on, to provide a visualization of the raw underlying data specific to the data source 119. This visualization may then be output by a data source 119 as video output to controller 101. In one example, display information elements may be hard-coded by a manufacturer of controller 101 or data sources 119. In one example, controller 101 may include a pixel selection editing tool program that enables a user of user interface 117 to manually specify display information elements. For example, a user may select a subset of the rendered data by selecting pixel coordinates. In another example, display information elements may be generated by an automated pattern recognition system. For example, controller 101 may include computer vision algorithms designed to automatically detect a portion of a video output from a data source 119 that may be automatically selected for inclusion in a display information element. In this way, controller 101 may manually and/or automatically capture at least a portion of each video screen output by each data source 119. Additional detail regarding the generation of display information elements is presented below with respect to FIG. 9.

User interface 117 enables the arbitrary placement of any display information element, from any source, in any arrangement to be simultaneously displayed on display 110. To that end, controller 101 may include WYSIWYG software stored in non-transitory memory 107 that when executed by processor 105 enables a user to create one or more display configurations, where the display configurations include an arrangement of display information elements. Each configuration of display information elements may be saved in memory 107 as a display macro for later use. The pre-configuration of a display macro using WYSIWYG software is described further herein and with regard to FIG. 3.

Multiple display macros may be utilized during a single medical procedure. For example, a user may establish a set of display macros for a single procedure, with each display macro emphasizing data from a particular, different data source. In some examples, each display macro may be related to an event during a medical procedure so that the display 110 automatically switches to an appropriate display macro when the corresponding event occurs. In other examples, user interface 117 may enable a user to manually switch between display macros, and even further may enable a user to adjust an arrangement of display information elements for a given display macro in real-time during the medical procedure.

In yet other examples, controller 101 may alert a user prior to changing a display macro or may alert a user that a more appropriate display macro should be used. For example, a particular display macro may not include a display information element that includes data from an echocardiograph (ECG) device. During a medical procedure, if the particular display macro without the ECG display information element is being displayed when a significant change in the ECG data occurs (for example, a patient's heartbeat drops below a threshold rate), controller 101 may alert a user of the significant change in ECG data. For example, controller 101 may display a message on display 110, emit a sound via a speaker, and so on. In some examples, controller 101 may automatically change the displayed display macro to a display macro that includes the ECG display information element.

Multi-element display system 100 may include a recording system 120 for recording procedure data in an event log. Recording system 120 may monitor data from sensors and detect events during a procedure. For example, recording system 120 may be directly or indirectly connected (via the controller 101, for example) to one or more data sources 119, such as a mapping system, an x-ray device, a stimulator, an ablation generator, and a plurality of sensors. In this way, for example, when ablation is in progress, the ablation generator may send data to the recording device 120. In some examples, a user of recording system 120 may manually enter information in an event log.

Recording system 120 may be operably coupled to the display controller 101, so that recording system 120 may send messages to the display controller 101. The messages may comprise information recorded in the event log. Display controller 101 may respond to the messages by changing a display macro shown on display 110. In this way, recording system 120 may be utilized to trigger a display macro change for different phases of a medical procedure.

Figure 2:
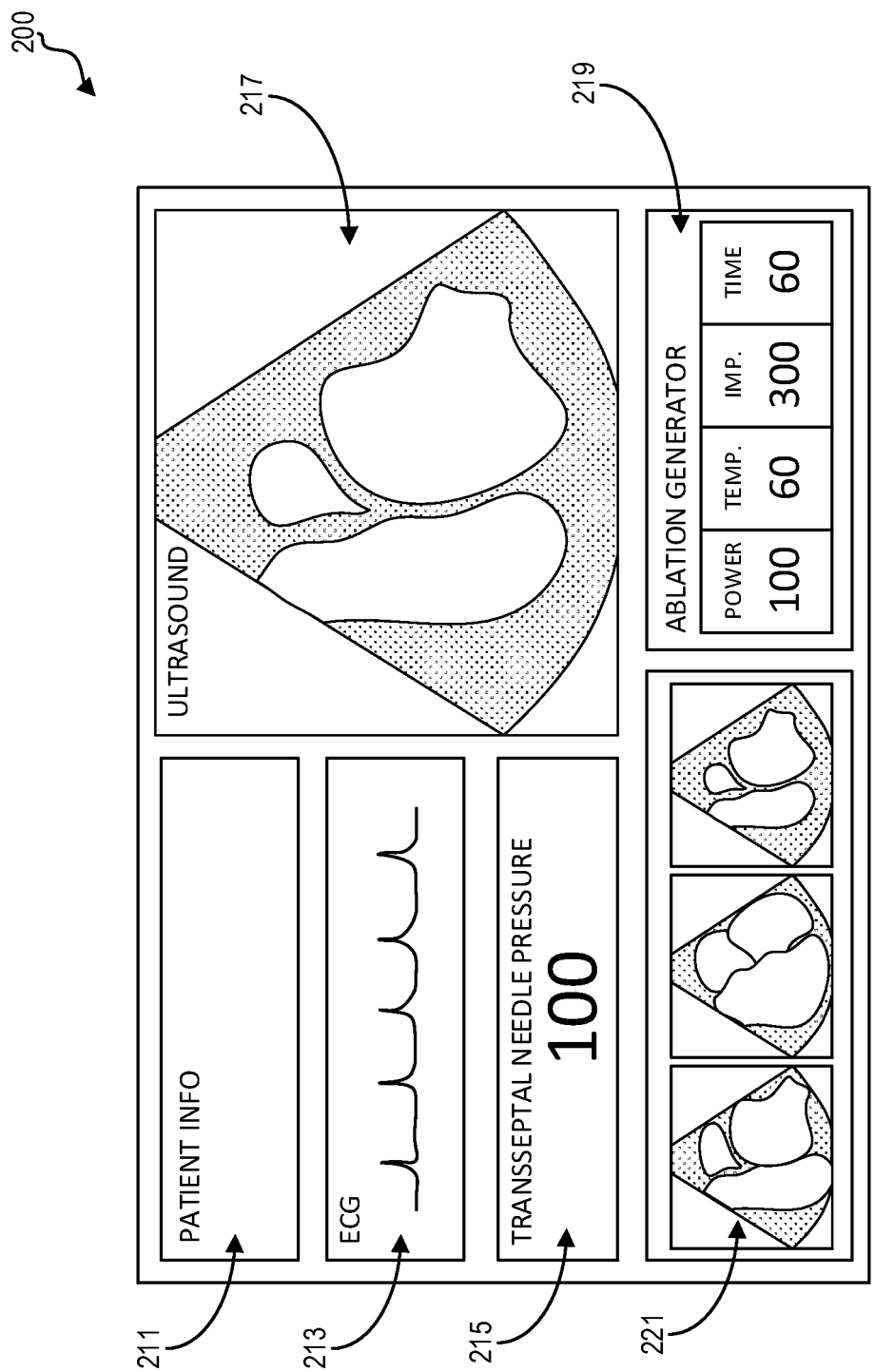
FIG. 2 shows an example multi-element display screen illustrating example aggregation of multiple system displays into one display screen.

FIG. 2 shows an example multi-element display screen 200 illustrating an example aggregation of multiple system displays into one display screen, such as on display 110 of FIG. 1. Multi-element display screen 200 may display a specified arrangement of a plurality of display information elements, where the plurality of display information elements may comprise a visualization of data from multiple data sources.

Display information elements may include, but are not limited to, visualizations of data such as patient information, electrocardiograph (ECG), transseptal needle pressure, ultrasound, ablation generator, ultrasound volume previews, and so on. For example, a patient information display information element 211 may include data regarding the patient, such as biographical information, medical history, portrait photograph, and so on. An ECG display information element 213 may include video output from an ECG device, or may include video synthesized from ECG data output from an ECG device. A transseptal needle pressure display information element 215 may include real-time pressure data for a transseptal needle. An ultrasound display information element 217 may include video output from an ultrasound device, or may include video synthesized from ultrasound data output from an ultrasound device. An ablation generator display information element 219 may include ablation generator settings data output from an ablation generator device. An ultrasound volume previews display information element 221 may include, for example, multiple alternate ultrasound views that may be selected by a user for more prominent display in the ultrasound display information element 217.

Display information elements may include visualized data that is stored in memory 107 rather than generated in real-time by a data source. For example, patient information display information element 211 may include textual data from a database in memory 107.

Figure 3:
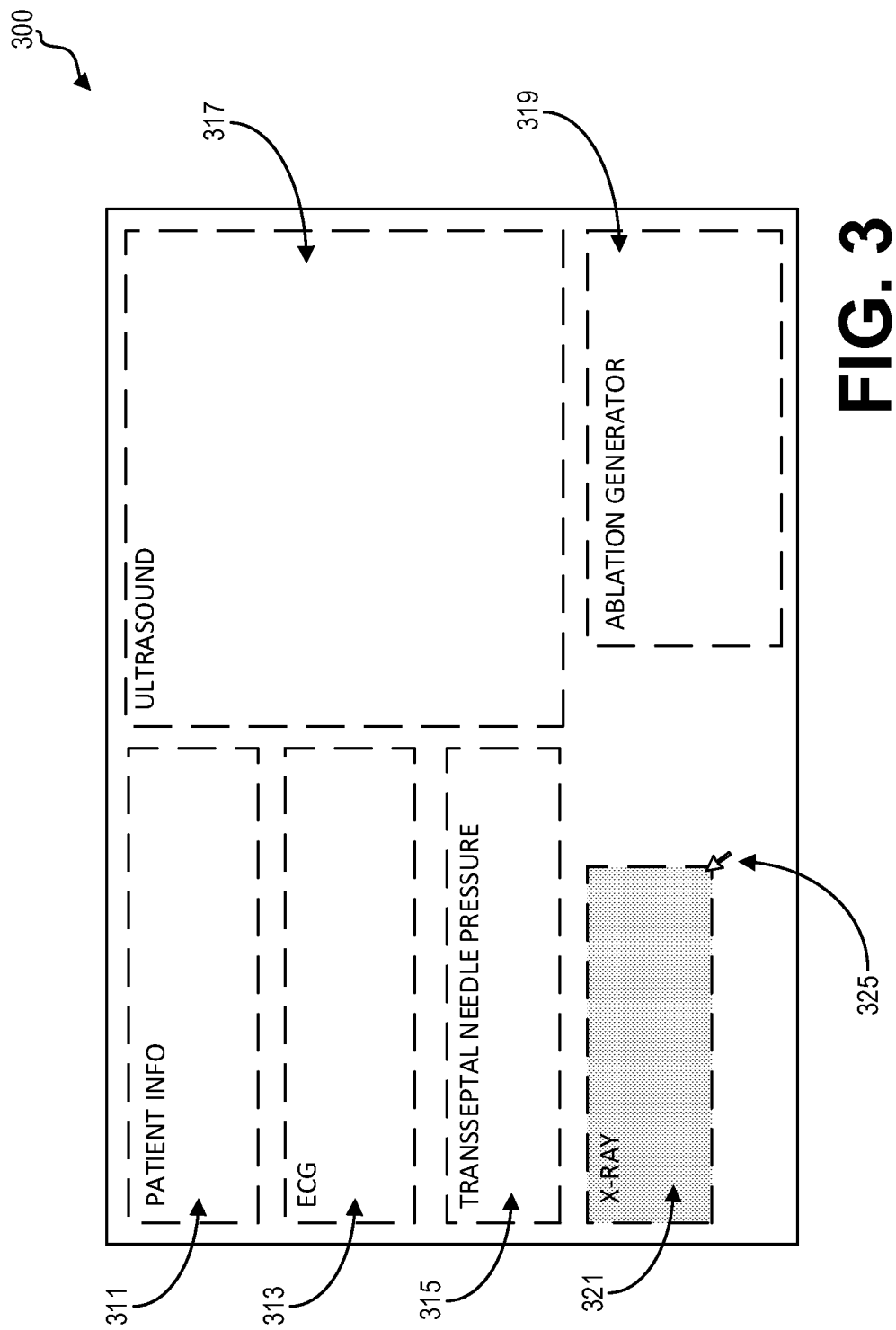
FIG. 3 shows an example what-you-see-is-what-you-get (WYSIWYG) interface for arranging display information elements.

FIG. 3 shows an example what-you-see-is-what-you-get (WYSIWYG) interface 300 for arranging display information elements. Interface 300 will be described herein with reference to the system depicted in FIG. 1, though it should be understood that the interface may be applied to other systems without departing from the scope of this disclosure. In particular, display controller 101 may include software in non-transitory memory 107 that when executed by processor 105 runs a program that displays WYSIWYG interface 300. User interface 117 may enable a user to utilize interface 300 to design a screen layout and save the screen layout as a display macro for later use.

Interface 300 may include a mock-up preview of a display screen 110 and may display an arrangement of display information elements. Display information elements may be added to the mock-up by, for example, placing a rectangular element onto interface 300 and associating the element with a particular display information element.

Interface 300 depicts a mock-up display macro similar to the display macro described hereinabove with regard to FIG. 2. In particular, the mock-up display macro includes a patient information display information element 311, an ECG display information element 313, a transseptal needle pressure display information element 315, an ultrasound display information element 317, and an ablation generator display information element 319. However, instead of an alternate ultrasound view display information element 221 as shown in FIG. 2, a user of WYSIWYG interface 300 has placed an x-ray display information element 321 in the same space on the screen.

User interface 117 may include a mouse for controlling a cursor 325 to place, resize, and rearrange display information elements on interface 300. As shown on interface 300, cursor 325 may resize the x-ray display information element 321 to cover the remaining available area on the screen. In this way, interface 300 enables a user to configure a display macro in a familiar way.

A size of a display information element may be based on the corresponding data signal. For example, the size of a display information element may be restricted by an input resolution of a video signal in order to preserve image quality. However, in some examples one or more image scaling techniques may be applied to a lower resolution video signal, if necessary, to display a video signal in a display information element that is larger than the input video resolution.

A shape of a display information element may be based on the corresponding data signal. In one example, the shape of a display information element may be restricted by an aspect ratio of a video signal in order to avoid cropping information from the video image. As such, a display information element box on interface 300 may have a fixed aspect ratio equal to the aspect ratio of a video that will populate the display information element box. In another example, the shape of a display information element may not be restricted by an aspect ratio of a video signal.

A user may save an arrangement of display information elements as a display macro for later use. In order to display the arrangement of display information elements saved as a display macro, display controller 101 executes the display macro, thereby assembling and arranging the multiple elements on a screen according to the display macro, and outputs the total screen to a display.

Figure 4:
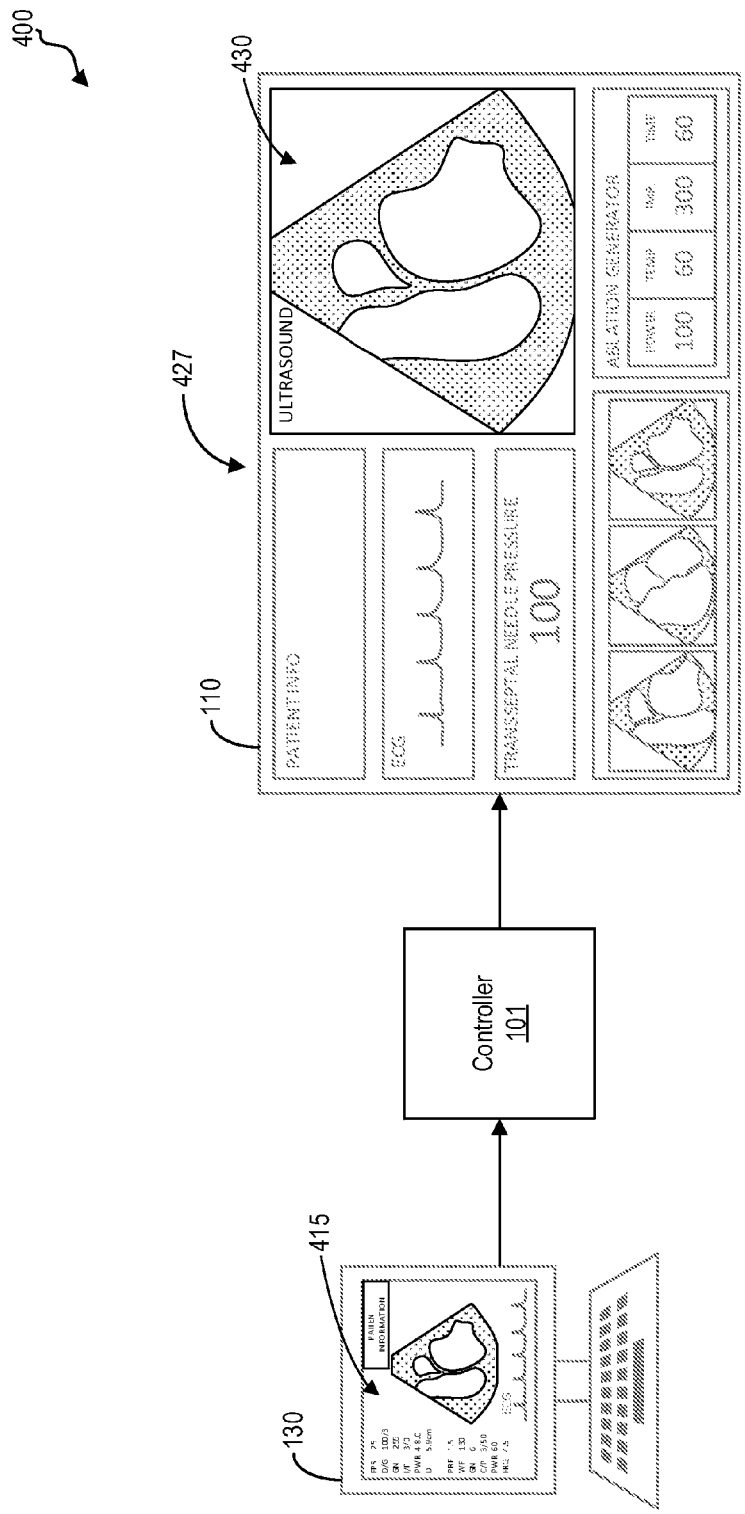
FIG. 4 shows an example diagram illustrating how video from multiple medical devices are aggregated on a single display screen.

FIG. 4 shows an example diagram 400 illustrating how video from a medical device may be aggregated with video from other medical devices on a single display screen. In particular, diagram 400 shows how video from an ultrasound system 130 may be displayed alongside other data on a separate large display 110.

For example, an ultrasound system 130 may collect ultrasound data via a transducer array probe (not shown) and use the ultrasound data to generate real-time ultrasound images of the internal tissue of a patient at a specified frame rate. The ultrasound system 130 may include a display screen for displaying the ultrasound images in succession at the specified frame rate, that is, as a video 415. Hence, in this example, an ultrasound system 130 may generate ultrasound video 415. In this way, a data source 119 may generate a visualization of raw data specific to the data source. The display screen of the ultrasound system may display additional information, such as patient information, patient heart rate (depicted in ECG output), imaging parameters and controls, and/or other information.

The ultrasound video 415 may be output to the display controller 101, for example, in the form of DVI output. The display controller 101 may then process the video signal comprising video 415 and output the processed video signal to a corresponding display information element 430. The display information element 430 may be one of multiple display information elements in a specified arrangement of a multiple element screen 427, displayed on a display screen 110. In some examples, the arrangement of the display information elements on the multiple element screen may be arranged according to an executed display macro.

Display controller 101 may utilize video screen capture techniques to capture and save the individual digital images of the video 415. Display controller 101 may place the captured video into a display information element. For multiple, dissimilar video sources, display controller 101 applies the process described above to each source to populate each display information element in a display macro. That is, display controller 101 overlays each screen to a display macro and sends the total output comprising the display macro to a display 110.

In some examples, display controller 101 may utilize geometrical techniques to project a digital video to a display information element to preserve the video. For example, techniques from affine geometry or projective geometry may preserve particular quantities, such as angles and/or length.

In some examples, one or more of the display information elements may be a 1:1 representation of the information output from the information source (e.g., the display output of the information source). For example, the display output from the ultrasound system 130 may be included in a display information element exactly as the display output displayed on the display screen of the ultrasound system, where the full display output is displayed. This may include all display information elements, from the top to the bottom of the display output and from the right to the left, with no information, images, video, text, etc., omitted.

However, in other examples, such as the example illustrated in FIG. 4, only a subset of the information output from the information source (e.g., a region of interest) may be displayed in a given display information element. As shown in FIG. 4, the information displayed on the display screen of the ultrasound system (e.g., the display output from the ultrasound system) includes patient information, ECG information, and imaging parameter information in addition to the actual video of the ultrasound images. However, in the multiple element screen 427, nearly all the information other than the video has been removed, to prevent the display of undesired, redundant, or otherwise unwanted information.

Thus, in some examples, only a region of interest of a display output is displayed in a multiple element screen. This includes only including a subset of the display output from a given source in the display information element of a multiple element screen configured for display on a display device, where the multiple element screen is sent from and populated by the controller. The subset excludes portions of the display output outside of the subset, but still configured for display on the display of the source. In one example, the subset may include only a central portion of the display output, with display information on all four sides of the display output excluded. In other examples, information from one, two, and/or three sides may be excluded, information from central portion(s) excluded, or other configuration.

The information (text, images, graphs, etc.) output from an external data source, such as the ultrasound system, may be configured for display on that data source's own display in a first configuration. The display information element selected for inclusion in a multiple element screen, configured for display on a common, large format display device, for example, may include the entirety of the information output from the external data source (and hence have the same configuration as the information displayed on the external data source's display) in one example. In another example, the display information element selected for inclusion in a multiple element screen may include only a subset of the information output from the external data source (and hence have a different configuration than the information displayed on the external data source's display). In addition, the region of interest actually displayed within the multiple element screen may vary from source device as the procedure progresses, such that the source device itself may help with defining the proper selection region to capture the information of interest.

In order to select a region of interest in the video output of a data source, a user may utilize a pixel-selection tool to define the region of interest, for example, the visualized ultrasound data. Controller 101 may then capture only the defined region of interest for inclusion in the corresponding display information element.

In one example, a defined region of interest may vary from a data source 119 as a case progresses, so that the data source 119 itself may adaptively define the proper selection region in order to capture the information of interest. For example, a user may indicate that he or she wants to capture the ultrasound picture region, and the picture region to pixel mapping may be continuously updated by the ultrasound system 130 if the screen layout of the ultrasound system 130 changes. In this way, a data source 119 may be hard-coded to intelligently provide an appropriate video output for aggregated display on a single screen.

In some examples, a data source 119 may not be hard-coded to provide an appropriate video output so that the entire data source display screen is output. A user may utilize controller 101 to define a region of interest on the data source display screen. Controller 101 may subsequently process the entire video output from the data source 119 using computer vision algorithms to adjust the selected region of interest should the screen layout of the data source 119 changes. In this way, controller 101 may intelligently capture a selected portion of a video output from a data source 119 for aggregated display on a single screen.

Figure 5:
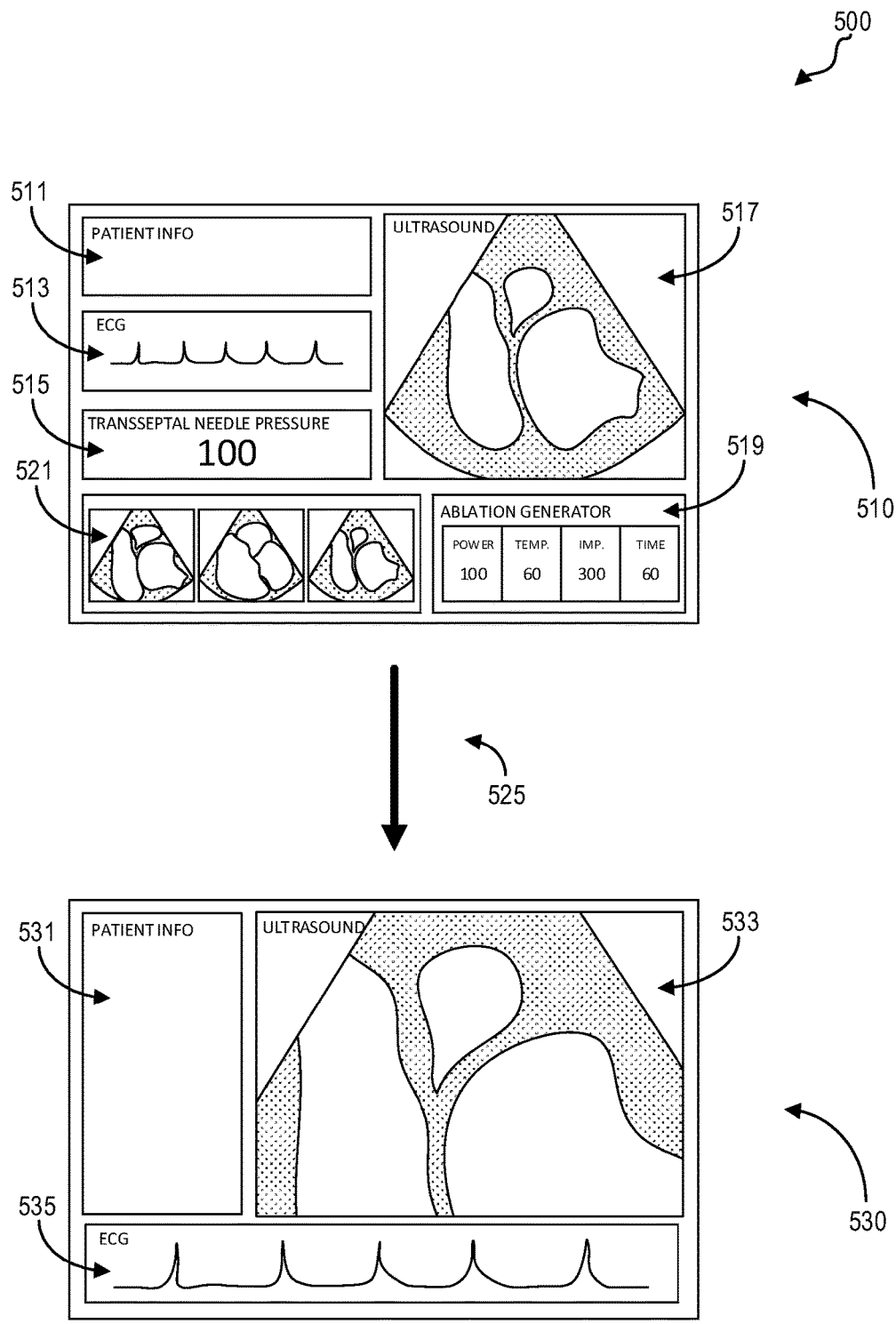
FIG. 5 shows an example macro workflow illustrating an example transition between display macros.

FIG. 5 shows an example macro workflow 500 illustrating an example transition 525 between display macros displayed on a display screen. In particular, macro workflow 500 depicts a transition 525 from a first arrangement of display information elements, or macro 510, to a second, different arrangement of display information elements, or macro 530. Macro workflow 500 will be described herein with reference to the system depicted in FIG. 1, though it should be understood that the method may be applied to other systems without departing from the scope of this disclosure. Macro workflow 500 may be carried out by processor 105, and may be stored as executable instructions in non-transitory memory 107 of the display controller 101.

Macro workflow 500 may comprise a collection of display macros and a set of events tied to each display macro so that when one event of the set of events occurs, the corresponding display macro is executed and the resulting screen is output to a display. In one example, one or more events of the set of events may comprise a reception of a message from recording system 120. The message may indicate that a first phase of a medical procedure has concluded and a second phase is beginning For example, display macro 510 may include display information elements relevant to the first phase while display macro 530 may include display information elements relevant to the second phase. Recording system 120 may, for example, automatically detect the end of the first phase and log the event in an event log, or a user of recording system 120 may manually enter the event into the event log. In either case, recording system 120 may send a message to display controller 101 indicating the logged event. In response to the message, display controller 101 may automatically change the displayed display macro from display macro 510 to display macro 530.

In one example, one or more events of the set of events may comprise a reception of specified data signal values from one of a data sources 119. For example, display macro 510 may include a transseptal needle pressure display information element 515, and transition 525 may be triggered by the transseptal needle pressure value decreasing below a threshold. The threshold may be specified such that below the threshold the transseptal needle is no longer being utilized, indicating that the transseptal phase of the procedure has concluded.

In another example, one or more events of the set of events may comprise a reception of a user command via user interface 117. For example, an event may comprise the reception of a verbal command via a microphone, a visual command (such as a particular physical gesture) via a camera, an electronic signal from a foot pedal controller, and so on.

Multiple display macros, such as display macro 510 and display macro 530, may include one or more of the same display information elements. For example, display macro 510 includes patient information display information element 511, ECG display information element 513, transseptal needle pressure display information element 515, ultrasound display information element 517, ablation generator display information element 519, and alternate ultrasound view display information element 521, while display macro 530 includes patient information display information element 531, ultrasound display information element 533, and ECG display information element 535. Patient information display information element 531 may include the same patient information as patient information display information element 511, but may include additional and/or different patient information as display information element 531 is larger than display information element 511 and can therefore include more information. The particular patient information displayed in display information element 511 and 531 and the particular arrangement of patient information may be pre-specified by a user.

In some examples, multiple display macros such as display macro 510 and display macro 530 may include the same display information elements but may display the display information elements with different arrangements and views. For example, note that both display macro 510 and display macro 530 include ultrasound display information elements 517 and 533, respectively. Ultrasound display information elements 517 and 533 may comprise the same ultrasound video signal from the same ultrasound device, however ultrasound display information element 533 shows a zoomed-in view of the ultrasound video. Ultrasound display information element 533 may be pre-configured to display a zoomed-in view of the ultrasound video. In some examples, the ultrasound video may be manually or automatically zoomed to an area of interest upon the transition to display macro 530. Furthermore, note that the aspect ratio of ultrasound display information element 533 is different than the aspect ratio of ultrasound display information element 517.

FIG. 6 is a flow chart illustrating a method 600 for adjusting a display arrangement according to a workflow protocol. As described above, a display device (such as a large display device 110 of FIG. 1) may be present in a procedure room, where a medical procedure is carried out on a patient by one or more practitioners. The display device may display one or more representations of data received from one or more sensors or devices monitoring or executing the procedure, in an arrangement predefined by the workflow protocol. Method 600 is described herein with reference to the system depicted in FIG. 1, though it should be understood that the method may be applied to other systems without departing from the scope of this disclosure. Method 600 may be carried out by processor 105 according to executable instructions stored in non-transitory memory 107 of the display controller 101.

At 605, method 600 includes receiving data from one or more data sources. The data sources may include the data sources 119 described above with respect to FIG. 1. In one non-limiting example, the data sources may include one or more of a mapping system, recording device, x-ray machine, ultrasound imaging device, heart monitor (e.g., ECG), body sensors (e.g., temperature, pressure, $CO_2$, etc.), and other suitable data sources. Data may be received from multiple data sources 119 as digital video signal. In some examples, data may be received as analog video signal, and method 600 may include converting the analog video signal to a digital video signal.

At 610, method 600 may include generating display information elements for each data source 119. Generating display information elements for each data source 119 may include capturing, processing, and placing the data in a display information element.

At 615, user input is received via a user interface. The user input may be made via a suitable manner, such as via input to a keyboard, mouse, and/or trackball, via eye gaze, voice commands, gestures, and/or other suitable input mechanisms.

At 620, method 600 includes receiving a workflow protocol selection. In one example, the workflow protocol selection may be made in response to a user input indicating a desired workflow protocol. The workflow protocol may include a series events to be performed during a specific procedure. For example, the user may indicate that the procedure is a heart ablation and select an appropriate workflow protocol for a heart ablation. The workflow protocol may be tailored for a specific patient or type of patient (e.g., child vs. adult), or it may be generic to all patients. In some examples, more than one workflow protocol may available for a specific procedure, and the user may select a desired workflow protocol that best fits the procedure that is to be performed.

The workflow protocol may include information to detect which event of the procedure is currently being performed. Further, the workflow protocol may also include one or more display macros that define an arrangement of display information elements on the display device. Each event of the workflow protocol may have a corresponding display macro, such that when a new event of the procedure is performed, the arrangement of elements displayed on the display device may change. Each display macro may define which display information elements are displayed on the display device, and in what position, size, orientation, focal point, etc. The workflow protocol may be predefined by the user, or by an alternate user, such as the manufacturer of the display controller, and may be stored in the memory of the display controller or other suitable device.

The workflow protocol may include a first display macro that defines the arrangement of displayed elements on the display device at the start of the procedure. Accordingly, at 625, the method selects a first display macro of the workflow protocol defining a first arrangement of display information elements on the display device and displays one or more display information elements on the display device in an arrangement according to the first display macro. The display information elements may include representations of the data signals received from the external data sources, and/or other suitable information, such as patient data. The first display macro may be defined in the workflow protocol as a default display macro, or may be specified as the first display macro for display.

At 630, method 600 includes identifying an event of the procedure based on the received data signals and/or based on user input. As explained above, the workflow protocol includes a series of events to be performed during the procedure, and information to detect when each event is actually performed during execution of the procedure. In order to detect and identify an event, the display controller may receive data signals that indicate a particular event is occurring. In one example, during a heart ablation, the controller may detect that the ablation is occurring when the ablation generator sends a signal to the controller. In some examples, the event may be additionally or alternatively identified based on user input. For example, a user may enter input via a keyboard, for example, indicating the ablation has started.

In some examples, the events of the procedure may be identified and recorded on a recording device coupled to the controller. In such examples, the recording device may send a notification to the controller identifying a current event of the procedure.

At 635, method 600 includes determining if an event is detected. Determining if an event is detected may comprise, for example, monitoring electronic communication with a recording system 120 for a message. Recording system 120 may automatically detect an event and send a message, or a user may manually input an event into recording system 120.

If a macro workflow event is not detected, method 600 continues to 640. At 640, method 600 includes maintaining the arrangement of display information elements according to the first display macro. Method 600 may then end.

Returning to 635, if an event is detected, method 600 continues to 645. At 645, method 600 includes displaying an arrangement of display information elements on a display screen according to a second display macro. The second display macro may be tied to the specific workflow event detected at 635. For example, a diagnosis display macro may be displayed during a diagnosis phase of a procedure while an emergency display macro may be displayed during an emergency phase. One workflow event may comprise a notification of the commencement of a diagnosis phase and thus the diagnosis display macro may be displayed, while a second workflow event may comprise a notification of an emergency phase and thus the emergency display macro may be displayed.

In another example, if the identified event includes activation of the ablation generator, a representation of the data signal sent from the ablation generator may be arranged in a center of the display device, made larger, or other adjustment. Further, in some examples, other display information elements not related to the current event, or deemed less important, may be removed, made smaller, moved to the side of the display, or other adjustments.

In further example, the procedure may include a cardiac output diagnosis procedure, where thermodilution analysis is performed. The thermodilution analysis may include the injection of a cold saline solution, for example, into the heart of a patient, and the temperature of the blood exiting the heart may be monitored by a temperature sensor. In such a procedure, when the system detects injection of the cold saline solution, the arrangement of display information elements may be adjusted so that data output from the temperature sensor is given prominence on the display screen.

As used herein, a procedure may refer to a medical procedure performed on a patient, and may be defined by a duration where the patient is monitored by the one or more data sources described above. For example, the procedure may commence when the patient is connected to one or more sensors or devices of a system (such as the system described above with respect to FIG. 1), when a recording system begins to log events of the procedure, and/or when an operator indicates the procedure has begun. Likewise, the procedure may end when the patient is disconnected from one or more sensors or devices, when the recording system stops logging events, and/or when an operator indicates the procedure is over. In more specific examples, the procedure may include coronary angiography or coronary catheterization, placement of pacemakers, heart ablation, and other medical procedures.

The procedure has an end result, such as the successful placement of a pacemaker or completion of an ablation. The procedure may include a series of events all related to reaching the end result of the procedure. The events may include placement of necessary devices on and within the patient, activation of specific devices, output from one or more sensors over time, and other actions that are defined as part of the procedure. The events may further include user-defined events, such as indication that a certain phase of the procedure has started or ended.

Thus, for each event of a procedure, a corresponding display macro may be selected according to a predefined workflow protocol. In this way, as the procedure progresses, the elements displayed on the display device may be adjusted so that the most pertinent data is displayed. The adjustment may include which elements are displayed, and/or in which position, at what size, which focal point is displayed (e.g., if the element is zoomed in or out), or other adjustments. The data signals received from the data sources may include video signals, such as from an ultrasound imaging device, Fluor, 2DICE, or other imaging devices. The data signals may also include signals from pressure, temperature, $CO_2$, or other body sensors, signals from electronic devices that output raw voltage signals, or other data signals. Such data signals may be converted into a suitable representation that may be displayed as a display information element, such as a graph that plots the data signal over time.

FIG. 7 shows a high-level flow chart illustrating an example method 700 for populating a display information element with video from an external data source. Method 700 will be described herein with reference to the system depicted in FIG. 1, though it should be understood that the method may be applied to other systems without departing from the scope of this disclosure. Method 700 may be carried out by processor 105, and may be stored as executable instructions in non-transitory memory 107 of the display controller 101.

Method 700 may begin at 705. At 705, method 700 may include receiving video data from a data source. In this way, method 700 may be executed by processor 105 as soon as a data source connected to display controller 101 is enabled.

At 710, method 700 may include capturing the video data. In examples where the video data from a data source is output as a digital video signal, capturing the video data may comprise converting the video data into a form that may be treated as a single data entity. In examples where the video data from a data source is output as an analog video, capturing the video data may comprise converting the analog video to digital video data and appropriately encoding the video data for output to display 110.

At 715, method 700 may include processing the video data. Processing the video data may include preparing the video data for display. Preparing the video data may include, for example, scaling the video, zooming in on a focal point of the video frame, and the like.

At 720, method 700 may include determining if the current display macro includes a display information element corresponding to the data source. The current display macro is a display macro currently being output to display 110. If the current display macro does not include a display information element corresponding to the data source, then method 700 may proceed to 725. At 725, method 700 may include saving the processed video data in a buffer in memory 107. In this way, video data from a data source may be prepared for display if a display macro including a display information element corresponding to the data source is executed and output to display 110. Method 700 may then end.

Returning to 720, if the current display macro includes a display information element corresponding to the data source, then method 700 may proceed to 730. At 730, method 700 may include populating a display information element with the processed video data. Method 700 may then end.

Method 700 may be applied to each video data source so that each display information element in a display macro may be populated with appropriately processed video prior to executing the display macro and outputting the resulting multi-element screen to a display 110.

FIG. 8 shows an example workflow protocol 800 illustrating an example transition 825 between display macros resulting in an adjustment of elements displayed on a display screen. In particular, workflow protocol 800 depicts a transition 825 from a first arrangement of display information elements, or macro 810, to a second, different arrangement of display information elements, or macro 830, in response to a detected ablation event, as described above.

Macro 810 includes patient information display information element 811, ECG display information element 813, transseptal needle pressure display information element 815, ultrasound display information element 817, ablation generator display information element 819, and alternate ultrasound view display information element 821. In response to identifying that an ablation has started (e.g., in response to detecting activation of the ablation generator), display macro 530 may be executed, resulting in adjustment of the arrangement of the elements displayed on the display device. For example, ablation generator display information element 819 is enlarged and moved to the center of the display device, so that is displayed more prominently. Less useful information, including the alternate ultrasound view display information element 821 and the transseptal needle pressure display information element 815, are removed for clarity. Other display information elements may also be adjusted; for example, the ECG display information element 813 may be moved to a different location of the display device.

In this way, a user may invoke a macro within his or her designed workflow model for a procedure. As the workflow is executed within the medical procedure, various display macros may be invoked within the procedural workflow as the user works through the procedure. Various pieces of equipment in the lab may be switched into the display at the appropriate point of the procedure, and their displayed data brought to the attention of the user. Meanwhile, devices that may be enabled but not providing meaningful or relevant data may be eliminated from the display so that the user may focus on the applicable data and images.

Thus, the macro enabled display elements described herein provide for macro control for display devices. The macros may be supported on a variety of workflow manager products that may support macros, or protocols for automation purposes. One example of such an environment is a hemodynamic recorder, an electrophysiology recorder, or other medical products such as Stress Test ECG, or other similar type systems.

A display macro may be designed according to a display designer, which enables the user to define a specific screen layout. The designer can take many forms dependent on the design of the display system. In the simplest form, it may include a series of tiles, which may be sized and arranged relative to the display screen. These tiles may be drop and drag, stretch and squeezed for scaling, and so forth. They may also be simple fixed format display options. Once a design has been created, or selected, the design may be associated to a display context moniker, e.g., the macro name. This is user selectable, and can be related to the context of the display sequence established by the user.

In one example, a transseptal macro may be used to provide visualization of transseptal puncture, where a needle is inserted into septum at chosen location to enable passage from right to left atrium. The display macro may facilitate visualization of Fluor, 2DICE Image, and transseptal needle pressure.

A display macro handler may enable translation from the received macro command and convert the macro command from the stored display definition to the physical display, including routing the received video feeds/and or data to the screen.

The macro may be executed according to macro display tags that are stored on the controlling medical workflow platform. These macros may be down loaded from the display manager, or alternatively simply typed in manually. The user can then invoke the macro within their designed workflow model for the procedure, or from a manual pull-down menu. Then as the macro is executed within the case, the various display macros may then be invoked within the procedural workflow as the user navigates the patient case. In this way, the various pieces of equipment in the lab may be switched in at the appropriate point of the case, and their displayed data brought to the attention of the user.

Extensions to this model can be made to invoke emergency displays in the event of device failure during the case using and emergency macro, instructing switch over to a back-up display. Other states that may require sequencing could be a clinical emergency, allowing the user to rapidly switch to a series of specific clinical emergency situations.

FIG. 9 shows a high-level flow chart illustrating an example method 900 for aggregating video from multiple, dissimilar sources into a single display. Method 900 is described herein with reference to the system depicted in FIG. 1, though it should be understood that the method may be applied to other systems without departing from the scope of this disclosure. Method 900 may be carried out by processor 105 according to executable instructions stored in non-transitory memory 107 of the display controller 101.

Method 900 may begin at 905. At 905, method 900 may include receiving a plurality of data signals, each data signal received from a respective external data source. The external data sources may comprise any device configured to output a data signal. For example, the external data sources may include, but are not limited to, an ultrasound system, an ablation generator, an echocardiograph system, a recording system (e.g., a recorder), an x-ray device, one or more pressure sensors, one or more temperature sensors, an endoscope, a pulse oximeter, a noninvasive blood pressure amplifier, gas analysis systems, one or more third-party devices, and the like.

At 910, method 900 may include capturing, from a first data signal of the plurality of data signals, digitized data into a first screen element. Capturing digitized data into a first screen element may be accomplished by a suitable video screen capture technology.

At 915, method 900 may include selecting at least a portion of the first screen element for inclusion in a first display information element. Selecting at least a portion of the first screen element may be accomplished manually or automatically. In one example, the first screen element may be automatically processed using edge detection algorithms to identify a dynamic portion of the first screen element. In another example, a user may manually select a portion of the first screen element to be included in the first display information element. In yet another example, a portion of the first screen element may be automatically selected according to a selection pre-specified by a user, e.g., according to a display macro as described above. In another example, the entirety of the first screen element may be included in the first display information element.

In some examples, the captured screen element may be dissected into multiple, atomic information elements that are selectable by a user or by an executed display macro. The atomic information elements may include pixels, or subsets of pixels, or other sub-set of the captured screen element.

When the portion of the screen element is selected, it may be selected according to a range of pixels input by a user or defined by the display macro, or by another suitable selection process.

At 920, method 900 may include capturing, from a second data signal of the plurality of data signals, digitized data into a second screen element. Capturing digitized data into a second screen element may be accomplished according to a suitable video screen capture technology.

At 925, method 900 may include selecting at least a portion of the second screen element for inclusion in a second display element. Selecting at least a portion of the second screen element may be accomplished manually or automatically. In one example, the second screen element may be automatically processed using edge detection algorithms to identify a dynamic portion of the second screen element. In another example, a user may manually select a portion of the second screen element to be included in the second display information element. In yet another example, a portion of the second screen element may be automatically selected according to a selection pre-specified by a user, e.g., according to a display macro as described above. In another example, the entirety of the second screen element may be included in the second display information element.

At 930, method 900 may include overlaying the first display information element and the second display information element onto a multiple element screen. The display information elements may be overlaid onto the multiple element screen according to a predetermined arrangement of display information elements, which may be determined according to user input or determined according to an executed display macro.

At 935, method 900 may include sending the multiple element screen to a display device. The display device may then display the multiple element screen including the first and second display information elements. In this way, data signals from multiple, dissimilar data sources may be displayed by the same display device. Method 900 may then end.

Thus, method 900 provides for the creation of a multiple element screen including one or more display information elements. The display information elements may be created on the source devices or at the controller, via data dependent rendering methods such as graphing, grid display, etc. This rendering provides the visualization of the raw underlying data specific to the source device in question. A subset of this rendered information is then selected, typically via pixel co-ordinates, for inclusion in the composited video output stream (e.g., in the multiple element screen).

FIG. 10 shows a pictorial diagram 1000 illustrating processes of a method for aggregating video from multiple, dissimilar sources into a single display. In particular, diagram 1000 is a pictorial depiction of the method described herein with regard to FIG. 9, and so relates to the creation of a multiple element screen including multiple display information elements and outputting the multiple element screen to a display. Diagram 1000 will be described herein with regard to the system shown in FIG. 1, though it should be understood that the method may be applied to other systems without departing from the scope of this disclosure.

Multiple data sources may generate video data and display the video data. For example, ECG system 134 and ultrasound device 130 may generate and display video such as ECG video 1005 and ultrasound video 1007, respectively. The data sources may output the video data to a display controller 101. Display controller 101 may capture each video output into a single screen element, such as captured ECG element 1015 and captured ultrasound element 1017. Display controller 101 may then populate a multiple element screen 1020 by inserting at least a portion of captured ECG element 1015 and at least a portion of captured ultrasound element 1017 into respective display information elements 1025 and 1027 of the multiple element screen 1020. In this way, ECG display information element 1025 may exclude irrelevant portions of the captured ECG element 1015. Such exclusion may automatically occur via edge detection, for example, or may be manually input by a user. Display controller may output the multiple element screen 1020 to a display 110. In this way, the original ECG video 1005 and ultrasound video 1007 may be displayed as an ECG video 1035 and an ultrasound video 1037 on the same display 110.

Thus, the approach disclosed according to the systems methods described above uses current technologies for screen capture, followed by intelligent image processing which dissects the acquired screens into sub-screen information elements. A user configuration control allows the selection of these elements in arbitrary placement of any element, from any source, in any arrangement on the available screen real estate. Coupled with available, large display screens, the user is offered a comprehensive solution to display of multiple data sources. In turn, with the use of display design macros, the user may readily replicate, change, and use various screen configurations as the situation demands. Furthermore, these changes may be driven by system wide lab events freeing the user of the obligation to manually control the display system. Input controls could be gaze, touch pad, foot pedal, table side control, voice, motion or virtually any other conceivable human input device.

The individual contributing systems have their display outputs routed to an image capture-aggregation computer (e.g., the controller described above). The display elements may be dissected at source by command or at receiver by program. The dissected elements are converted to display information elements (DIE). These may be hard coded by the manufacturer, or specified by the user using a pixel selection editing tool, or automated pattern recognition system. In doing so the DIE is created, and encapsulated to form the user defined/manufacturer defined display information element. In turn the element can then be referenced by the user and directed to the display using WYSIWIG editor.

This approach aims to addresses the issue of a system having more display generating capability than physical screen(s) to display. Further, in the case of existing large screen display systems, the design goes further to eliminate redundant or unnecessary information. It reduces the need for suboptimal scaling, and other data distorting transformations. Specifically, it enables the creation of custom displays where only context applicable data is displayed, and in order of procedural significance, in a low cost manner.

The systems and methods described may be implemented in a variety of environments, including but not limited to medical procedure environments, such as interventional suites, operating rooms, and case review scenarios, or other environments that require significant concurrent information and data and/or where dissimilar data sets need to be visualized concurrently to support diagnosis and detection.

The approach described herein eliminates the need for multiple screens and allows the user to assimilate information over a physically wide span, while removing extraneous unimportant display elements, including menus, static data, unrelated information and other visual noise.

The technical effect of the disclosure may include the creation of user-defined custom displays aggregating multiple data signals, where only context applicable data is displayed. Another technical effect of the disclosure may include the creation and execution of user-defined custom display macros comprising a display workflow, wherein a different user-defined custom display aggregating multiple data signals may be displayed during different phases of a medical procedure. Another technical effect of the disclosure may include execution of the custom display aggregating multiple data signals in an order of procedural significance.

One embodiment for a computing device is provided. The computing device comprises at least one input configured to receive data from one or more data sources; a user interface to receive user input; and instructions to identify an event of a procedure based on one or more of data received from the one or more data sources and user input received via the user interface, and arrange one or more display information elements on a display device based on the identified event and a workflow protocol.

In an example, the data comprises a video signal. In another example, the data comprises one or more of a temperature, pressure, heart rate, and ablation generation signal.

The one or more display information elements may be arranged according to a selected display macro, the selected display macro selected based on the identified event and workflow protocol. The display macro may define one or more of a presence, position, size, and focal point of the one or more display information elements on the display device, and each display information element may comprise a representation of data from a respective data source. The workflow protocol may comprise a predefined series events of the procedure and one or more display macros that each correspond to a given event of the procedure.

The computing device may include further instructions to select a workflow protocol responsive to user input. In an example, the procedure is a medical procedure.

In an example, the event is a first event, the one or more display information elements are arranged according to a first display macro, and the computing device includes further instructions to identify a second event of the procedure, and arrange the one or more information display elements according to a second display macro selected based on the second event and the workflow protocol.

Another embodiment relates to a system, comprising: a controller; a plurality of external data sources each operably coupled to the controller; a display device operably coupled to the controller; and instructions on the controller to identify each event of a procedure based on data received from the plurality of external devices and select a display device element arrangement based on a current event.

The plurality of external data sources may comprise one or more of a mapping system, recording device, x-ray machine, ultrasound imaging device, stimulator, ablation generator, balloon inflation device, and one or more sensors. The recording device may record each event of the procedure and send a notification identifying the current event to the controller.

A display device element arrangement may include a display macro that defines one or more of a position, size, and focal point of one or more display information elements. The one or more display information elements may each be configured to display a representation of data received from an external data source of the plurality of data sources.

The instructions on the controller may include instructions to execute a workflow protocol that defines a respective display device element arrangement for each event of the procedure. Each event of the procedure may be identified based on the data received from the plurality of data sources and further based on user input to the controller.

An embodiment for a method comprises displaying on a display device one or more display information elements according to a first arrangement of a workflow protocol; receiving a plurality of data signals, each data signal sent from an external data source; receiving user input; identifying an event of a procedure, the event identified based on one or more of the received data signals and user input; selecting a second arrangement from the workflow protocol based on the identified event; and displaying on the display device one or more display information elements according to the second arrangement.

The workflow protocol may comprise a predefined series of display macros that each correspond to a given event of the procedure, and each display macro may define an arrangement of one or more display information elements on the display device, each display information element including a representation of a respective data signal.

In an example, the procedure comprises a heart ablation, one of the plurality of external data sources comprises an ablation generator, the event comprises activation of the ablation generator, and selecting the second arrangement comprises selecting a display macro that includes a display information element of a representation of the data signal received from the ablation generator. The second display macro may adjust one or more of a position, size, and/or focal point of one or more display information elements respective to a position, size, and/or focal point of the one or more display information elements arranged according to the first display macro.

In an example, the procedure comprises a cardiac output diagnosis procedure, the external data source comprises a temperature sensor, the event comprises a thermodilution analysis including injection of cold liquid into a heart of a patient, and selecting the second arrangement comprises selecting a display macro that includes a display information element of a representation of the data signal received from the temperature sensor.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:

automatically arranging, via a display controller, a first set of display information elements according to a first display macro of a workflow protocol, the workflow protocol comprising a predefined series of display macros including the first display macro that each correspond to a given event of a procedure, each display macro defining an arrangement of display information elements for display, the procedure comprising a heart ablation;

displaying, on a display device, the first set of display information elements arranged according to the first display macro;

receiving, at the display controller, a plurality of data signals, each data signal sent from a respective external medical device, one data signal of the plurality of data signals comprising a data signal from an ablation generator;

receiving, at the display controller, user input;

identifying, with the display controller, an event of the procedure, the event comprising activation of the ablation generator identified based on the data signal from the ablation generator;

automatically selecting, with the display controller, a second display macro from the predefined series of display macros of the workflow protocol based on the identified event, the second display macro including a second set of display information elements that includes at least a representation of the data signal received from the ablation generator; and displaying, on the display device, the second set of display information elements according to the second display macro, each display information element including a representation of a respective data signal.

2. The method of claim 1, wherein automatically arranging the first set of display information elements according to the first display macro comprises automatically processing a first data signal from the plurality of data signals into a first screen element and processing the first screen element into a first display information element using an edge detection algorithm to capture a dynamic portion of the first screen element, and arranging the first display information element according to the first display macro, and further comprising, prior to displaying on the display device the one or more display information elements according to the first display macro, selecting the first display macro from the predefined series of display macros based on the user input.

3. The method of claim 2, wherein the first display macro includes the first display information element and the second display macro excludes the first display information element.

4. The method of claim 2, wherein the second display macro adjusts a position and/or a size of the first display information element respective to a position, size, and/or focal point of the first display information element arranged according to the first display macro.

5. A computing device, comprising:

a universal interface coupled to one or more medical devices, the one or more medical devices including an ablation generator;

a user interface to receive user input;

a processor in electronic communication with the one or more medical devices and with a display device; and memory storing instructions executable by the processor to:

identify an event of a predefined series of events of a medical procedure based on data signals received from the one or more medical devices, the medical procedure defined by a duration where a patient is monitored by the one or more medical devices, the event including activation of the ablation generator identified based on a data signal received from the ablation generator, automatically arrange one or more display information elements for display according to a first arrangement based on the identified event and a workflow protocol, including adjusting each of a size and a position of the one or more display information elements based on the identified event, the one or more display information elements representing at least a portion of the data signals received from the one or more medical devices including at least a representation of the data signal received from the ablation generator, and send the one or more display information elements arranged according to the first arrangement to the display device.

6. The computing device of claim 5, wherein one or more of the data signals comprise a video signal, wherein the event is a first event, and wherein the instructions are executable to identify a second event responsive to receiving a message from a recording system, the recording system configured to record information in an event log and generate the message responsive to the recorded information, and wherein the recorded information includes the data signals from the one or more medical devices.

7. The computing device of claim 5, wherein the data signals further comprise a temperature, a pressure, and/or a heart rate signal.

8. The computing device of claim 5, wherein the instructions to arrange the one or more display information elements according to the first arrangement based on the identified event and the workflow protocol include instructions to automatically select a display macro from a set of display macros based on the identified event and the workflow protocol, and arrange the one or more display information elements according to the selected display macro, wherein the selected display macro defines the size and the position of the one or more display information elements and further defines a presence and a focal point of the one or more display information elements, each display information element comprising a representation of data from a respective medical device.

9. The computing device of claim 8, wherein the workflow protocol comprises the predefined series of events of the medical procedure and the set of display macros, each display macro corresponding to a given event of the medical procedure, and wherein the memory stores instructions executable to, for a first data signal received from a first medical device, process the first data signal into a first display information element using computer vision to adjust a selected region of interest of the first display information element as the first data signal changes.

10. The computing device of claim 8, wherein the identified event is a first event, the selected display macro is a first display macro, and wherein the memory stores further instructions executable to identify a second event of the predefined series of events of the medical procedure, and automatically arrange the one or more display information elements according to a second display macro selected based on the second event and the workflow protocol, where the second display macro includes the one or more display information elements being displayed at a different size and/or position than when displayed according to the first display macro, and send the one or more display information elements arranged according to the second display macro to the display device.

11. The computing device of claim 5, wherein the memory stores further instructions executable to select the workflow protocol responsive to user input.

12. The computing device of claim 5, wherein the instructions to arrange the one or more display information elements according to the first arrangement based on the identified event and the workflow protocol include instructions to adjust a size of a first display information element from a first, smaller size to a second, larger size, and to adjust a position of the first display information element from a first position to a second position, wherein the first display information element includes a representation of a data signal and the data signal is the same when the first display information element is displayed at the first size and when the first display information element is displayed at the second size, and wherein the first display macro includes an additional version of the first display information element at the first size and at a third position, different than the second position.

13. A system, comprising:
a controller including a processor comprising one or more physical devices;
a plurality of external medical devices each operably coupled to the controller the plurality of external medical devices including an ablation generator;
a display device operably coupled to the controller; and
instructions on the controller to:
identify each of a plurality of events of a procedure based on data received from the plurality of external medical devices and automatically select a display device element arrangement based on a current event of the plurality of events, the display device element arrangement defining a size and a position for each of one or more display information elements on the display device, where the plurality of events includes at least activation of the ablation generator identified based on first data received from the ablation generator and when the activation of the ablation generator is detected, the display device element arrangement defines a size and a position for a first display information element that represents the first data; and
output the one or more display information elements arranged according to the display device element arrangement to the display device.

14. The system of claim 13, wherein the plurality of external medical devices further comprises a mapping system, a recording device, an x-ray machine, an ultrasound imaging device, a stimulator, a balloon inflation device, and/or one or more sensors.

15. The system of claim 14, wherein the recording device records each event of the procedure and sends a notification identifying the current event to the controller.

16. The system of claim 13, wherein the display device element arrangement further defines one or more of a focal point and a magnification of the one or more display information elements, including the display device element arrangement defining a focal point of the first display information element independent of an original display context of a source display system of the ablation generator.

17. The system of claim 16, wherein the one or more display information elements are each configured to display a representation of data received from an external medical device of the plurality of external medical devices.

18. The system of claim 13, wherein the instructions on the controller include instructions to execute a workflow protocol that defines a respective display device element arrangement for each event of the procedure.

19. The system of claim 13, wherein each event of the procedure is identified based on the data received from the plurality of external medical devices and further based on user input to the controller.

* * * * *